US012685288B2

(12) United States Patent
   Pais de Arruda

(10) Patent No.: US 12,685,288 B2
(45) Date of Patent: Jul. 21, 2026

(54) HYBRID TOMATO PLANT NAMED EL ROSILLO

(71) Applicant: HM.CLAUSE, INC., Davis, CA (US)

(72) Inventor: Marcio Pais de Arruda, Davis, CA (US)

(73) Assignee: HM.CLAUSE, INC., Davis, CA (US)

( * ) Notice: Subject to any disclaimer, the term of this patent is extended or adjusted under 35 U.S.C. 154(b) by 260 days.

(21) Appl. No.: 18/498,524

(22) Filed: Oct. 31, 2023

(65) Prior Publication Data

US 2025/0134057 A1    May 1, 2025

(51) Int. Cl.
   *A01H 5/08*       (2018.01)
   *A01H 1/00*       (2006.01)
   *A01H 6/82*       (2018.01)

(52) U.S. Cl.
   CPC .............. *A01H 6/825* (2018.05); *A01H 1/00* (2013.01); *A01H 5/08* (2013.01)

(58) Field of Classification Search
   None
   See application file for complete search history.

(56) References Cited

U.S. PATENT DOCUMENTS 11,344,002 B1 *   5/2022   Kuehn ................... A01H 6/825

OTHER PUBLICATIONS

Arruda et al., "Hybrid Tomato Plant Named Red Coral," U.S. Appl. No. 17/867,112, filed Jul. 18, 2022, 73 pages.
Jiang, C., "Hybrid Tomato Plant Named HM 8507," U.S. Appl. No. 18/173,553, filed Feb. 23, 2023, 69 pages.
Lepeltier, J., "Hybrid Tomato Plant Named Curioso," U.S. Appl. No. 18/476,068, filed Sep. 27, 2023, 70 pages.
Lepeltier, J., "Hybrid Tomato Plant Named Intuitivo," U.S. Appl. No. 18/475,991, filed Sep. 27, 2023, 70 pages.
Zamudio, P., "Hybrid Tomato Plant Named HMC44440," U.S. Appl. No. 18/056,617, filed Nov. 17, 2022, 72 pages.
Zamudio, P., "Hybrid Tomato Plant Named HMC44441," U.S. Appl. No. 18/056,620, filed Nov. 17, 2022, 72 pages.

* cited by examiner

*Primary Examiner* — Phuong T Bui
(74) *Attorney, Agent, or Firm* — McKee, Voorhees & Sease, PLC

(57)                ABSTRACT

A hybrid tomato plant, designated EL ROSILLO is disclosed. The disclosure relates to the seeds of hybrid tomato designated EL ROSILLO, to the plants and plant parts of hybrid tomato designated EL ROSILLO, and to methods for producing a tomato plant by crossing the hybrid tomato EL ROSILLO with itself or another tomato plant.

24 Claims, No Drawings

HYBRID TOMATO PLANT NAMED EL ROSILLO

TECHNICAL FIELD

The present disclosure relates to the field of agriculture, to new and distinctive hybrid tomato plants, such as a hybrid plant designated EL ROSILLO and to methods of making and using such hybrids.

BACKGROUND

Tomato is an important and valuable vegetable crop. Thus, a continuing goal of plant breeders is to develop stable, high yielding tomato hybrids that are agronomically sound or unique. The reasons for this goal are to maximize the amount of fruit produced on the land used (yield) as well as to improve the fruit appearance, the fruit shape and size, eating and processing qualities and/or the plant agronomic and horticultural qualities. To accomplish this goal, the tomato breeder must select and develop tomato plants that have the traits that result in superior parental lines that combine to produce superior hybrids.

SUMMARY

The following embodiments and aspects thereof are described in conjunction with systems, tools and methods which are meant to be exemplary, not limiting in scope.

According to the disclosure, in some embodiments there is provided a novel hybrid tomato designated EL ROSILLO, also interchangeably referred to as 'hybrid tomato EL ROS-ILLO', 'tomato hybrid EL ROSILLO' or 'EL ROSILLO'.

This disclosure thus relates to the seeds of hybrid tomato designated EL ROSILLO, to the plants or parts of hybrid tomato designated EL ROSILLO, to plants or parts thereof comprising all of the physiological and morphological characteristics of hybrid tomato designated EL ROSILLO or parts thereof, and/or having all of the physiological and morphological characteristics of hybrid tomato designated EL ROSILLO, and/or having one or more of or all of the characteristics of hybrid tomato designated EL ROSILLO including but not limited to as determined at the 5% significance level when grown in the same environmental conditions, and/or having one or more of the physiological and morphological characteristics of hybrid tomato designated EL ROSILLO including but not limited to as determined at the 5% significance level when grown in the same.

Thus, in some embodiments, the breeding methods of the present disclosure include breeding with one or more TILL-ING plant lines with one or more identified mutations.

ix. Mutation Breeding

Mutation breeding is another method of introducing new variation and subsequent traits into tomato plants. Mutations that occur spontaneously or are artificially induced can be useful sources of variability for a plant breeder. The goal of artificial mutagenesis is to increase the rate of mutation for a desired characteristic. Mutation rates can be increased by many different means or mutating agents including tempera-ture, long-term seed storage, tissue culture conditions, radia-tion (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, eth-yleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding can be found in W. R. Fehr, 1993, Principles of Cultivar Develop-ment, Macmillan Publishing Co.

New breeding techniques such as the ones involving the uses of engineered nucleases to enhance the efficacy and precision of gene editing in combination with oligonucle-otides including, but not limited to Zinc Finger Nucleases (ZFN), TAL effector nucleases (TALENs), chemical nucle-ases, meganucleases, homing nucleases and clustered regu-larly interspaced short palindromic repeats (CRISPR)-asso-ciated endonuclease Cas (CRISPR-Cas) system (using such as Cas9, Cas12a/Cpf1, Cas13/C2c2, CasX and CasY) shall also be used to generate genetic variability and introduce new traits into tomato varieties.

x. Double Haploids and Chromosome Doubling

One way to obtain homozygous plants without the need to cross two parental lines followed by a long selection of the segregating progeny, and/or multiple backcrossing is to produce haploids and then double the chromosomes to form doubled haploids. Haploid plants can occur spontaneously, or may be artificially induced via chemical treatments or by crossing plants with inducer lines (Seymour et al. 2012, PNAS vol. 109, pg. 4227-4232; Zhang et al., 2008 Plant Cell Rep. December 27 (12) 1851-60). The production of haploid progeny can occur via a variety of mechanisms which can affect the distribution of chromosomes during gamete for-mation. The chromosome complements of haploids some-times double spontaneously to produce homozygous doubled haploids (DHs). Mixoploids, which are plants which contain cells having different ploidies, can sometimes arise and may represent plants that are undergoing chromo-some doubling so as to spontaneously produce doubled haploid tissues, organs, shoots, floral parts or plants. Another common technique is to induce the formation of double haploid plants with a chromosome doubling treatment such as colchicine (El-Hennawy et al., 2011 Vol 56, issue 2 μg. 63-72; Doubled Haploid Production in Crop Plants 2003 edited by Maluszynski ISBN 1-4020-1544-5). The produc-tion of doubled haploid plants yields highly uniform inbred lines and is especially desirable as an alternative to sexual inbreeding of longer-generation crops. By producing doubled haploid progeny, the number of possible gene combinations for inherited traits is more manageable. Thus, an efficient doubled haploid technology can significantly reduce the time and the cost of inbred and cultivar devel-opment.

xi. Protoplast Fusion

In another method for breeding plants, protoplast fusion can also be used for the transfer of trait-conferring genomic material from a donor plant to a recipient plant. Protoplast fusion is an induced or spontaneous union, such as a somatic hybridization, between two or more protoplasts (cells of which the cell walls are removed by enzymatic treatment) to produce a single bi- or multi-nucleate cell. The fused cell that may even be obtained with plant species that cannot be interbred in nature is tissue cultured into a hybrid plant exhibiting the desirable combination of traits.

xii. Embryo Rescue

Alternatively, embryo rescue may be employed in the transfer of resistance-conferring genomic material from a donor plant to a recipient plant. Embryo rescue can be used as a procedure to isolate embryos from crosses to rapidly move to the next generation of backcrossing or selfing or wherein plants fail to produce viable seed. In this process, the fertilized ovary or immature seed of a plant is tissue cultured to create new plants (see Pierik, 1999, *In Vitro*

*Culture of Higher Plants*, Springer, ISBN 079235267X, 978-0792352679, which is incorporated herein by reference in its entirety).

Gene Editing/Genome Editing

Gene editing (or Genome editing) technologies. Breeding and selection schemes of the present disclosure can include crosses with plant lines that have undergone genome editing. In some embodiments, the breeding and selection methods of the present disclosure are compatible with plants that have been modified using any gene and/or genome editing tool, including, but not limited to: ZFNs, TALENs, CRISPR-Cas, and Mega nuclease technologies. In some embodiments, persons having skill in the art will recognize that the breeding methods of the present disclosure are compatible with many other gene editing technologies. In some embodiments, the present disclosure teaches gene-editing technologies can be applied for a single locus conversion, for example, conferring tomato plant with herbicide resistance. In some embodiments, the present disclosure teaches that the single locus conversion is an artificially mutated gene or nucleotide sequence that has been modified through the use of breeding techniques taught herein.

In some embodiments, the breeding and selection methods of the present disclosure are compatible with plants that have been modified through Zinc Finger Nucleases. Three variants of the ZFN technology are recognized in plant breeding (with applications ranging from producing single mutations or short deletions/insertions in the case of ZFN-1 and -2 techniques up to targeted introduction of new genes in the case of the ZFN-3 technique); 1) ZFN-1: Genes encoding ZFNs are delivered to plant cells without a repair template. The ZFNs bind to the plant DNA and generate site specific double-strand breaks (DSBs). The natural DNA-repair process (which occurs through nonhomologous end-joining, NHEJ) leads to site specific mutations, in one or only a few base pairs, or to short deletions or insertions; 2) ZFN-2: Genes encoding ZFNs are delivered to plant cells along with a repair template homologous to the targeted area, spanning a few kilo base pairs. The ZFNs bind to the plant DNA and generate site-specific DSBs. Natural gene repair mechanisms generate site-specific point mutations e.g. changes to one or a few base pairs through homologous recombination and the copying of the repair template; and 3) ZFN-3: Genes encoding ZFNs are delivered to plant cells along with a stretch of DNA which can be several kilo base pairs long and the ends of which are homologous to the DNA sequences flanking the cleavage site. As a result, the DNA stretch is inserted into the plant genome in a site-specific manner.

In some embodiments, the breeding and selection methods of the present disclosure are compatible with plants that have been modified through Transcription activator-like (TAL) effector nucleases (TALENs). TALENs are polypeptides with repeat polypeptide arms capable of recognizing and binding to specific nucleic acid regions. By engineering the polypeptide arms to recognize selected target sequences, the TAL nucleases can be used to direct double stranded DNA breaks to specific genomic regions. These breaks can then be repaired via recombination to edit, delete, insert, or otherwise modify the DNA of a host organism. In some embodiments, TALENs are used alone for gene editing (e.g., for the deletion or disruption of a gene). In other embodiments, TALs are used in conjunction with donor sequences and/or other recombination factor proteins that will assist in the Non-homologous end joining (NHEJ) process to replace the targeted DNA region. For more information on the TAL-mediated gene editing compositions and methods of the present disclosure, see U.S. Pat. Nos. 8,440,432; 8,450, 471; 8,586,526; 8,586,363; 8,592,645; 8,697,853; 8,704, 041; 8,921,112; and 8,912,138, each of which is hereby incorporated in its entirety for all purposes.

In some embodiments, the breeding and selection methods of the present disclosure are compatible with plants that have been modified through Clustered Regularly Interspaced Short Palindromic Repeats (CRISPR) or CRISPR-associated (Cas) gene editing tools. CRISPR proteins were originally discovered as bacterial adaptive immunity systems which protected bacteria against viral and plasmid invasion. There are at least three main CRISPR system types (Type I, II, and III) and at least 10 distinct subtypes (Makarova, K. S., et. al., Nat Rev Microbiol. 2011 May 9; 9 (6): 467-477). Type I and III systems use Cas protein complexes and short guide polynucleotide sequences to target selected DNA regions. Type II systems rely on a single protein (e.g. Cas9) and the targeting guide polynucleotide, where a portion of the 5' end of a guide sequence is complementary to a target nucleic acid. For more information on the CRISPR gene editing compositions and methods of the present disclosure, see U.S. Pat. Nos. 8,697,359; 8,889,418; 8,771,945; and 8,871,445, each of which is hereby incorporated in its entirety for all purposes.

In some embodiments, the breeding and selection methods of the present disclosure are compatible with plants that have been modified through meganucleases. In some embodiments, meganucleases are engineered endonucleases capable of targeting selected DNA sequences and inducing DNA breaks. In some embodiments, new meganucleases targeting specific regions are developed through recombinant techniques which combine the DNA binding motifs from various other identified nucleases. In other embodiments, new meganucleases are created through semi-rational mutational analysis, which attempts to modify the structure of existing binding domains to obtain specificity for additional sequences. For more information on the use of meganucleases for genome editing, see Silva et al., 2011 Current Gene Therapy 11 µg 11-27; and Stoddard et al., 2014 Mobile DNA 5 µg 7, each of which is hereby incorporated in its entirety for all purposes.

Plant Transformation

Tomato plants of the present disclosure, such as 'EL ROSILLO' can be further modified by introducing one or more transgenes which when expressed lead to desired phenotypes. The most common method for the introduction of new genetic material into a plant genome involves the use of living cells of the bacterial pathogen *Agrobacterium tumefaciens* to literally inject a piece of DNA, called transfer or T-DNA, into individual plant cells (usually following wounding of the tissue) where it is targeted to the plant nucleus for chromosomal integration. There are numerous patents governing *Agrobacterium* mediated transformation and particular DNA delivery plasmids designed specifically for use with *Agrobacterium*—for example, U.S. Pat. No. 4,536,475, EP0265556, EP0270822, WO8504899, WO8603516, U.S. Pat. No. 5,591,616, EP0604662, EP0672752, WO8603776, WO9209696, WO9419930, WO9967357, U.S. Pat. No. 4,399,216, WO8303259, U.S. Pat. No. 5,731,179, EP068730, WO9516031, U.S. Pat. Nos. 5,693,512, 6,051,757 and EP904362A1. *Agrobacterium*-mediated plant transformation involves as a first step the placement of DNA fragments cloned on plasmids into living *Agrobacterium* cells, which are then subsequently used for transformation into individual plant cells. *Agrobacterium*-mediated plant transformation is thus an indirect plant transformation method. Methods of *Agrobacterium*-mediated plant transformation that involve using vectors with no T-DNA are also well known to those skilled in the art and can have applicability in the present disclosure. See, for example, U.S. Pat. No. 7,250,554, which utilizes P-DNA instead of T-DNA in the transformation vector.

Direct plant transformation methods using DNA have also been reported. The first of these to be reported historically is electroporation, which utilizes an electrical current applied to a solution containing plant cells (M. E. Fromm et al., Nature, 319, 791 (1986); H. Jones et al., Plant Mol. Biol., 13, 501 (1989) and H. Yang et al., *Plant Cell Reports,* 7, 421 (1988). Another direct method, called "biolistic bombardment", uses ultrafine particles, usually tungsten or gold, that are coated with DNA and then sprayed onto the surface of a plant tissue with sufficient force to cause the particles to penetrate plant cells, including the thick cell wall, membrane and nuclear envelope, but without killing at least some of them (U.S. Pat. Nos. 5,204,253, and 5,015,580). A third direct method uses fibrous forms of metal or ceramic consisting of sharp, porous or hollow needle-like projections that literally impale the cells, and also the nuclear envelope of cells. Both silicon carbide and aluminum borate whiskers have been used for plant transformation (Mizuno et al., 2004; Petolino et al., 2000; U.S. Pat. No. 5,302,523 U.S. application No. 20040197909) and also for bacterial and animal transformation (Kaepler et al., 1992; Raloff, 1990; Wang, 1995). There are other methods reported, and undoubtedly, additional methods will be developed. However, the efficiencies of each of these indirect or direct methods in introducing foreign DNA into plant cells are invariably extremely low, making it necessary to use some method for selection of only those cells that have been transformed, and further, allowing growth and regeneration into plants of only those cells that have been transformed.

For efficient plant transformation, a selection method must be employed such that whole plants are regenerated from a single transformed cell and every cell of the transformed plant carries the DNA of interest. These methods can employ positive selection, whereby a foreign gene is supplied to a plant cell that allows it to utilize a substrate present in the medium that it otherwise could not use, such as mannose or xylose (for example, refer U.S. Pat. Nos. 5,767, 378; and 5,994,629). More typically, however, negative selection is used because it is more efficient, utilizing selective agents such as herbicides or antibiotics that either kill or inhibit the growth of nontransformed plant cells and reducing the possibility of chimeras. Resistance genes that are effective against negative selective agents are provided on the introduced foreign DNA used for the plant transformation. For example, one of the most popular selective agents used is the antibiotic kanamycin, together with the resistance gene neomycin phosphotransferase (nptII), which confers resistance to kanamycin and related antibiotics (see, for example, Messing & Vierra, *Gene* 19:259-268 (1982); Bevan et al., *Nature* 304:184-187 (1983)). However, many different antibiotics and antibiotic resistance genes can be used for transformation purposes (U.S. Pat. Nos. 5,034,322, 6,174,724 and 6,255,560). In addition, several herbicides and herbicide resistance genes have been used for transformation purposes, including the bar gene, which confers resistance to the herbicide phosphinothricin (White et al., *Nucl Acids Res* 18:1062 (1990), Spencer et al., *Theor Appl Genet* 79:625-631 (1990), U.S. Pat. Nos. 4,795,855, 5,378, 824 and 6,107,549). In addition, the dhfr gene, which confers resistance to the anticancer agent methotrexate, has been used for selection (Bourouis et al., *EMBO J.* 2 (7): 1099-1104 (1983).

Genes can be introduced in a site directed fashion using homologous recombination. Homologous recombination permits site specific modifications in endogenous genes and thus inherited or acquired mutations may be corrected, and/or novel alterations may be engineered into the genome. Homologous recombination and site-directed integration in plants are discussed in, for example, U.S. Pat. Nos. 5,451, 513, 5,501,967 and 5,527,695.

Methods of producing transgenic plants are well known to those of ordinary skill in the art. Transgenic plants can now be produced by a variety of different transformation methods including, but not limited to, electroporation; microinjection; microprojectile bombardment, also known as particle acceleration or biolistic bombardment; viral-mediated transformation; and *Agrobacterium*-mediated transformation. See, for example, U.S. Pat. Nos. 5,405,765; 5,472,869; 5,538,877; 5,538,880; 5,550,318; 5,641,664; and 5,736,369; and International Patent Application Publication Nos. WO/2002/038779 and WO/2009/117555; Lu et al., (Plant Cell Reports, 2008, 27:273-278); Watson et al., Recombinant DNA, Scientific American Books (1992); Hinchee et al., Bio/Tech. 6:915-922 (1988); McCabe et al., Bio/Tech. 6:923-926 (1988); Toriyama et al., Bio/Tech. 6:1072-1074 (1988); Fromm et al., Bio/Tech. 8:833-839 (1990); Mullins et al., Bio/Tech. 8:833-839 (1990); Hiei et al., Plant Molecular Biology 35:205-218 (1997); Ishida et al., Nature Biotechnology 14:745-750 (1996); Zhang et al., Molecular Biotechnology 8:223-231 (1997); Ku et al., Nature Biotechnology 17:76-80 (1999); and, Raineri et al., Bio/Tech. 8:33-38 (1990)), each of which is expressly incorporated herein by reference in their entirety.

Microprojectile bombardment is also known as particle acceleration, biolistic bombardment, and the gene gun (Biolistic® Gene Gun). The gene gun is used to shoot pellets that are coated with genes (e.g., for desired traits) into plant seeds or plant tissues in order to get the plant cells to then express the new genes. The gene gun uses an actual explosive (0.22 caliber blank) to propel the material. Compressed air or steam may also be used as the propellant. The Biolistic® Gene Gun was invented in 1983-1984 at Cornell University by John Sanford, Edward Wolf, and Nelson Allen. It and its registered trademark are now owned by E. I. du Pont de Nemours and Company. Most species of plants have been transformed using this method.

*Agrobacterium tumefaciens* is a naturally occurring bacterium that is capable of inserting its DNA (genetic information) into plants, resulting in a type of injury to the plant known as crown gall. Most species of plants can now be transformed using this method, including cucurbitaceous species. A transgenic plant formed using *Agrobacterium* transformation methods typically contains a single gene on one chromosome, although multiple copies are possible. Such transgenic plants can be referred to as being hemizygous for the added gene. A more accurate name for such a plant is an independent segregant, because each transformed plant represents a unique T-DNA integration event (U.S. Pat. No. 6,156,953). A transgene locus is generally characterized by the presence and/or absence of the transgene. A heterozygous genotype in which one allele corresponds to the absence of the transgene is also designated hemizygous (U.S. Pat. No. 6,008,437).

General genetic transformation methods, and specific methods for transforming certain plant species (e.g., maize) are described in U.S. Pat. Nos. 4,940,838, 5,464,763, 5,149, 645, 5,501,967, 6,265,638, 4,693,976, 5,635,381, 5,731,179, 5,693,512, 6,162,965, 5,693,512, 5,981,840, 6,420,630, 6,919,494, 6,329,571, 6,215,051, 6,369,298, 5,169,770, 5,376,543, 5,416,011, 5,569,834, 5,824,877, 5,959,179, 5,563,055, and 5,968,830, each of which is incorporated herein by reference in its entirety for all purposes.

Non-limiting examples of methods for transforming tomato plants and tomato tissue culture methods are described in McCormick, S. (Transformation of Tomato With *Agrobacterium tumefaciens*," Plant Tissue Culture Manual B6:1-9 (Kluwer Academic Publishers 1991)); and U.S. Pat. No. 5,569,831, each of which is herein incorporated by reference in its entirety for all purposes. The transformation can be physical, chemical and/or biological.

Grafting

Grafting is a process that has been used for many years in crops such as cucurbitacea, but only more recently for some commercial watermelon and tomato production. Grafting may be used to provide a certain level of resistance to telluric pathogens such as *Phytophthora* or to certain nematodes. Grafting is therefore intended to prevent contact between the plant or variety to be cultivated and the infested soil. The variety of interest used as the graft or scion, optionally an F1 hybrid, is grafted onto the resistant plant used as the rootstock. The resistant rootstock remains healthy and provides, from the soils, the normal supply for the graft that it isolates from the diseases. In some recent developments, it has also been shown that some rootstocks are also able to improve the agronomic value for the grafted plant and in particular the equilibrium between the vegetative and generative development that are always difficult to balance in tomato cultivation.

Breeding Evaluation

Each breeding program can include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested per se and in hybrid combination and compared to appropriate standards in environments representative of the commercial target area(s). The best lines are candidates for use as parents in new commercial cultivars; those still deficient in a few traits may be used as parents to produce new populations for further selection or in a backcross program to improve the parent lines for a specific trait.

In some embodiments, the plants are selected on the basis of one or more phenotypic traits. Skilled persons will readily appreciate that such traits include any observable characteristic of the plant, including for example growth rate, vigor, plant health, maturity, branching, plant height, leaf coverage, weight, total yield, color, taste, sugar levels, aroma, changes in the production of one or more compounds by the plant (including for example, metabolites, proteins, drugs, carbohydrates, oils, and any other compounds).

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

It should be appreciated that in certain embodiments, plants may be selected based on the absence, suppression or inhibition of a certain feature or trait (such as an undesirable feature or trait) as opposed to the presence of a certain feature or trait (such as a desirable feature or trait).

Selecting plants based on genotypic information is also envisaged (for example, including the pattern of plant gene expression, genotype, or presence of genetic markers). Where the presence of one or more genetic marker is assessed, the one or more marker may already be known and/or associated with a particular characteristic of a plant; for example, a marker or markers may be associated with an increased growth rate or metabolite profile. This information could be used in combination with assessment based on other characteristics in a method of the disclosure to select for a combination of different plant characteristics that may be desirable. Such techniques may be used to identify novel quantitative trait loci (QTLs). By way of example, plants may be selected based on growth rate, size (including but not limited to weight, height, leaf size, stem size, branching pattern, or the size of any part of the plant), general health, survival, tolerance to adverse physical environments and/or any other characteristic, as described herein before.

Further non-limiting examples include selecting plants based on: speed of seed germination; quantity of biomass produced; increased root, and/or leaf/shoot growth that leads to an increased yield (fruit) or biomass production; effects on plant growth that results in an increased seed yield for a crop; effects on plant growth which result in an increased yield; effects on plant growth that lead to an increased resistance or tolerance to disease including fungal, viral or bacterial diseases, to *mycoplasma*, or to pests such as insects, mites or nematodes in which damage is measured by decreased foliar symptoms such as the incidence of bacterial or fungal lesions, or area of damaged foliage or reduction in the numbers of nematode cysts or galls on plant roots, or improvements in plant yield in the presence of such plant pests and diseases; effects on plant growth that lead to increased metabolite yields; effects on plant growth that lead to improved aesthetic appeal which may be particularly important in plants grown for their form, color or taste, for example the color intensity of tomato exocarp (skin) of said fruit.

Molecular Breeding Evaluation Techniques

Selection of plants based on phenotypic or genotypic information may be performed using techniques such as, but not limited to: high through-put screening of chemical components of plant origin, sequencing techniques including high through-put sequencing of genetic material, differential display techniques (including DDRT-PCR, and DD-PCR), nucleic acid microarray techniques, RNA-seq (Whole Transcriptome Shotgun Sequencing), qRTPCR (quantitative real time PCR).

In one embodiment, the evaluating step of a plant breeding program involves the identification of desirable traits in progeny plants. Progeny plants can be grown in, or exposed to conditions designed to emphasize a particular trait (e.g. drought conditions for drought tolerance, lower temperatures for freezing tolerant traits). Progeny plants with the highest scores for a particular trait may be used for subsequent breeding steps.

In some embodiments, plants selected from the evaluation step can exhibit a 1%, 5%, 10%, 15%, 20%, 25%, 30%, 35%, 40%, 45%, 50%, 55%, 60%, 65%, 70%, 75%, 80%, 85%, 90%, 95%, 100%, 120% or more improvement in a particular plant trait compared to a control plant.

In other embodiments, the evaluating step of plant breeding comprises one or more molecular biological tests for genes or other markers. For example, the molecular biological test can involve probe hybridization and/or amplification of nucleic acid (e.g., measuring nucleic acid density by Northern or Southern hybridization, PCR) and/or immunological detection (e.g., measuring protein density, such as precipitation and agglutination tests, ELISA (e.g., Lateral Flow test or DAS-ELISA), Western blot, Radioimmune Assay (RIA), immune labeling, immunosorbent electron microscopy (ISEM), and/or dot blot).

The procedure to perform a nucleic acid hybridization, an amplification of nucleic acid (e.g., PCR, RT-PCR) or an immunological detection (e.g., precipitation and agglutination tests, ELISA (e.g., Lateral Flow test or DAS-ELISA), Western blot, RIA, immunogold or immunofluorescent labeling, immunosorbent electron microscopy (ISEM), and/or dot blot tests) are performed as described elsewhere herein and well-known by one skilled in the art.

In one embodiment, the evaluating step comprises PCR (semi-quantitative or quantitative), wherein primers are used to amplify one or more nucleic acid sequences of a desirable gene, or a nucleic acid associated with said gene, or a desirable trait (e.g., a co-segregating nucleic acid, or other marker).

In another embodiment, the evaluating step comprises immunological detection (e.g., precipitation and agglutination tests, ELISA (e.g., Lateral Flow test or DAS-ELISA), Western blot, RIA, immuno labeling (gold, fluorescent, or other detectable marker), immunosorbent electron microscopy (ISEM), and/or dot blot), wherein one or more gene or marker-specific antibodies are used to detect one or more desirable proteins. In one embodiment, said specific antibody is selected from the group consisting of polyclonal antibodies, monoclonal antibodies, antibody fragments, and combination thereof.

Reverse Transcription Polymerase Chain Reaction (RT-PCR) can be utilized in the present disclosure to determine expression of a gene to assist during the selection step of a breeding scheme. It is a variant of polymerase chain reaction (PCR), a laboratory technique commonly used in molecular biology to generate many copies of a DNA sequence, a process termed "amplification". In RT-PCR, however, RNA strand is first reverse transcribed into its DNA complement (complementary DNA, or cDNA) using the enzyme reverse transcriptase, and the resulting cDNA is amplified using traditional or real-time PCR. An exemplary PCR scheme is presented below.

RT-PCR utilizes a pair of primers, which are complementary to a defined sequence on each of the two strands of the cDNA. These primers are then extended by a DNA polymerase and a copy of the strand is made after each cycle, leading to logarithmic amplification.

RT-PCR includes three major steps. The first step is the reverse transcription (RT) where RNA is reverse transcribed to cDNA using a reverse transcriptase and primers. This step is very important in order to allow the performance of PCR since DNA polymerase can act only on DNA templates. The RT step can be performed either in the same tube with PCR (one-step PCR) or in a separate one (two-step PCR) using a temperature between 40° C. and 60° C., depending on the properties of the reverse transcriptase used.

The next step involves the denaturation of the dsDNA at 95° C., so that the two strands separate and the primers can bind again at lower temperatures and begin a new chain reaction. Then, the temperature is decreased until it reaches the annealing temperature which can vary depending on the set of primers used, their concentration, the probe and its concentration (if used), and the cations concentration. The main consideration, of course, when choosing the optimal annealing temperature is the melting temperature (Tm) of the primers and probes (if used). The annealing temperature chosen for a PCR depends directly on length and composition of the primers. This is the result of the difference of hydrogen bonds between A-T (2 bonds) and G-C (3 bonds). An annealing temperature about 5 degrees below the lowest Tm of the pair of primers is usually used.

The final step of PCR amplification is the DNA extension from the primers which is done by the thermostable Taq DNA polymerase usually at 72° C., which is the optimal temperature for the polymerase to work. The length of the incubation at each temperature, the temperature alterations and the number of cycles are controlled by a programmable thermal cycler. The analysis of the PCR products depends on the type of PCR applied. If a conventional PCR is used, the PCR product is detected using for example agarose gel electrophoresis or other polymer gel like polyacrylamide gels and ethidium bromide (or other nucleic acid staining).

Conventional RT-PCR is a time-consuming technique with important limitations when compared to real time PCR techniques. This combined with the fact that ethidium bromide has low sensitivity, yields results that are not always reliable. Moreover, there is an increased cross-contamination risk of the samples since detection of the PCR product requires the post-amplification processing of the samples. Furthermore, the specificity of the assay is mainly determined by the primers, which can give false-positive results. However, the most important issue concerning conventional RT-PCR is the fact that it is a semi or even a low quantitative technique, where the amplicon can be visualized only after the amplification ends.

Real time RT-PCR provides a method where the amplicons can be visualized as the amplification progresses using a fluorescent reporter molecule. There are three major kinds of fluorescent reporters used in real time RT-PCR, general nonspecific DNA Binding Dyes such as SYBR Green I, TaqMan Probes and Molecular Beacons (including Scorpions).

For example, the real time PCR thermal cycler has a fluorescence detection threshold, below which it cannot discriminate the difference between amplification generated signal and background noise. On the other hand, the fluorescence increases as the amplification progresses and the instrument performs data acquisition during the annealing step of each cycle. The number of amplicons will reach the detection baseline after a specific cycle, which depends on the initial concentration of the target DNA sequence. The cycle at which the instrument can discriminate the amplification generated fluorescence from the background noise is called the threshold cycle (Ct). The higher is the initial DNA concentration, the lower its Ct will be.

Other forms of nucleic acid detection can include next generation sequencing methods such as DNA SEQ or RNA SEQ using any known sequencing platform including, but not limited to: Roche 454, Solexa Genome Analyzer, AB SOLID, Illumina GA/HiSeq, Ion PGM, Mi Seq, among others (Liu et al,. 2012 Journal of Biomedicine and Bio-technology Volume 2012 ID 251364; Franca et al., 2002 Quarterly Reviews of Biophysics 35 µg. 169-200; Mardis 2008 Genomics and Human Genetics vol. 9 µg. 387-402).

In other embodiments, nucleic acids may be detected with other high throughput hybridization technologies including microarrays, gene chips, LNA probes, nanoStrings, and fluorescence polarization detection among others.

In some embodiments, detection of markers can be achieved at an early stage of plant growth by harvesting a small tissue sample (e.g., branch, or leaf disk). This approach is preferable when working with large populations as it allows breeders to weed out undesirable progeny at an early stage and conserve growth space and resources for progeny which show more promise. In some embodiments the detection of markers is automated, such that the detec-tion and storage of marker data is handled by a machine. Recent advances in robotics have also led to full service analysis tools capable of handling nucleic acid/protein marker extractions, detection, storage and analysis.

Quantitative Trait Loci

Breeding schemes of the present application can include crosses between donor and recipient plants. In some embodiments, said donor plants contain a gene or genes of interest which may confer the plant with a desirable pheno-type. The recipient line can be an elite line having certain favorable traits for commercial production. In one embodi-ment, the elite line may contain other genes that also impart said line with the desired phenotype. When crossed together, the donor and recipient plant may create a progeny plant with combined desirable loci which may provide quantita-tively additive effect of a particular characteristic. In that case, QTL mapping can be involved to facilitate the breeding process.

A QTL (quantitative trait locus) mapping can be applied to determine the parts of the donor plant's genome confer-ring the desirable phenotype, and facilitate the breeding methods. Inheritance of quantitative traits or polygenic inheritance refers to the inheritance of a phenotypic char-acteristic that varies in degree and can be attributed to the interactions between two or more genes and their environ-ment. Though not necessarily genes themselves, quantitative trait loci (QTLs) are stretches of DNA that are closely linked to the genes that underlie the trait in question. QTLs can be molecularly identified to help map regions of the genome that contain genes involved in specifying a quantitative trait. This can be an early step in identifying and sequencing these genes.

Typically, QTLs underlie continuous traits (those traits that vary continuously, e.g. yield, height, level of resistance to virus, etc.) as opposed to discrete traits (traits that have two or several character values, e.g. smooth vs. wrinkled peas used by Mendel in his experiments). Moreover, a single phenotypic trait is usually determined by many genes. Consequently, many QTLs are associated with a single trait.

A quantitative trait locus (QTL) is a region of DNA that is associated with a particular phenotypic trait. Knowing the number of QTLs that explains variation in the phenotypic trait tells about the genetic architecture of a trait. It may tell that a trait is controlled by many genes of small effect, or by a few genes of large effect or by a several genes of small effect and few genes of larger effect.

Another use of QTLs is to identify candidate genes underlying a trait. Once a region of DNA is identified as contributing to a phenotype, it can be sequenced. The DNA sequence of any genes in this region can then be compared to a database of DNA for genes whose function is already known.

In a recent development, classical QTL analyses are combined with gene expression profiling i.e. by DNA microarrays. Such expression QTLs (e-QTLs) describes cis- and trans-controlling elements for the expression of often disease-associated genes. Observed epistatic effects have been found beneficial to identify the gene responsible by a cross-validation of genes within the interacting loci with metabolic pathway and scientific literature databases.

QTL mapping is the statistical study of the alleles that occur in a locus and the phenotypes (physical forms or traits) that they produce (see, Meksem and Kahl, *The handbook of plant genome mapping: genetic and physical mapping,* 2005, Wiley-VCH, ISBN 3527311165, 9783527311163). Because most traits of interest are governed by more than one gene, defining and studying the entire locus of genes related to a trait gives hope of understanding what effect the genotype of an individual might have in the real world.

Statistical analysis is required to demonstrate that differ-ent genes interact with one another and to determine whether they produce a significant effect on the phenotype. QTLs identify a particular region of the genome as containing one or several genes, i.e. a cluster of genes that is associated with the trait being assayed or measured. They are shown as intervals across a chromosome, where the probability of association is plotted for each marker used in the mapping experiment.

To begin, a set of genetic markers must be developed for the species in question. A marker is an identifiable region of variable DNA. Biologists are interested in understanding the genetic basis of phenotypes (physical traits). The aim is to find a marker that is significantly more likely to co-occur with the trait than expected by chance, that is, a marker that has a statistical association with the trait. Ideally, they would be able to find the specific gene or genes in question, but this is a long and difficult undertaking. Instead, they can more readily find regions of DNA that are very close to the genes in question. When a QTL is found, it is often not the actual gene underlying the phenotypic trait, but rather a region of DNA that is closely linked with the gene.

For organisms whose genomes are known, one might now try to exclude genes in the identified region whose function is known with some certainty not to be connected with the trait in question. If the genome is not available, it may be an option to sequence the identified region and determine the putative functions of genes by their similarity to genes with known function, usually in other genomes. This can be done using BLAST, an online tool that allows users to enter a primary sequence and search for similar sequences within the BLAST database of genes from various organisms.

Another interest of statistical geneticists using QTL map-ping is to determine the complexity of the genetic architec-ture underlying a phenotypic trait. For example, they may be interested in knowing whether a phenotype is shaped by many independent loci, or by a few loci, and how those loci interact. This can provide information on how the phenotype may be evolving.

Molecular markers are used for the visualization of dif-ferences in nucleic acid sequences. This visualization is possible due to DNA-DNA hybridization techniques (RFLP) and/or due to techniques using the polymerase chain reac-tion (e.g. STS, SNPs, microsatellites, AFLP). All differences between two parental genotypes will segregate in a mapping population based on the cross of these parental genotypes. The segregation of the different markers may be compared and recombination frequencies can be calculated. The recombination frequencies of molecular markers on different chromosomes are generally 50%. Between molecular markers located on the same chromosome the recombination frequency depends on the distance between the markers. A low recombination frequency usually corresponds to a low distance between markers on a chromosome. Comparing all recombination frequencies will result in the most logical order of the molecular markers on the chromosomes. This most logical order can be depicted in a linkage map (Paterson, 1996, Genome Mapping in Plants. R. G. Landes, Austin.). A group of adjacent or contiguous markers on the linkage map that is associated to a reduced disease incidence and/or a reduced lesion growth rate pinpoints the position of a QTL.

The nucleic acid sequence of a QTL may be determined by methods known to the skilled person. For instance, a nucleic acid sequence comprising said QTL or a resistance-conferring part thereof may be isolated from a donor plant by fragmenting the genome of said plant and selecting those fragments harboring one or more markers indicative of said QTL. Subsequently, or alternatively, the marker sequences (or parts thereof) indicative of said QTL may be used as (PCR) amplification primers, in order to amplify a nucleic acid sequence comprising said QTL from a genomic nucleic acid sample or a genome fragment obtained from said plant. The amplified sequence may then be purified in order to obtain the isolated QTL. The nucleotide sequence of the QTL, and/or of any additional markers comprised therein, may then be obtained by standard sequencing methods.

One or more such QTLs associated with a desirable trait in a donor plant can be transferred to a recipient plant to incorporate the desirable trait(s) into progeny plants by transferring and/or breeding methods.

In one embodiment, an advanced backcross QTL analysis (AB-QTL) is used to discover the nucleotide sequence or the QTLs responsible for the resistance of a plant. Such method was proposed by Tanksley and Nelson in 1996 (Tanksley and Nelson, 1996, Advanced backcross QTL analysis: a method for simultaneous discovery and transfer of valuable QTL from un-adapted germplasm into elite breeding lines. *Theor Appl Genet* 92:191-203) as a new breeding method that integrates the process of QTL discovery with variety development, by simultaneously identifying and transferring useful QTL alleles from un-adapted (e.g., land races, wild species) to elite germplasm, thus broadening the genetic diversity available for breeding. AB-QTL strategy was initially developed and tested in tomato, and has been adapted for use in other crops including rice, maize, wheat, pepper, barley, and bean. Once favorable QTL alleles are detected, only a few additional marker-assisted generations are required to generate near isogenic lines (NILs) or introgression lines (ILs) that can be field tested in order to confirm the QTL effect and subsequently used for variety development.

Isogenic lines in which favorable QTL alleles have been fixed can be generated by systematic backcrossing and introgressing of marker-defined donor segments in the recurrent parent background. These isogenic lines are referred to as near isogenic lines (NILs), introgression lines (ILs), backcross inbred lines (BILs), backcross recombinant inbred lines (BCRIL), recombinant chromosome substitution lines (RCSLs), chromosome segment substitution lines (CSSLs), and stepped aligned inbred recombinant strains (STAIRSs). An introgression line in plant molecular biology is a line of a crop species that contains genetic material derived from a similar species. ILs represent NILs with relatively large average introgression length, while BILs and BCRILs are backcross populations generally containing multiple donor introgressions per line. As used herein, the term "introgression lines or ILs" refers to plant lines containing a single marker defined homozygous donor segment, and the term "pre-ILs" refers to lines which still contain multiple homozygous and/or heterozygous donor segments.

To enhance the rate of progress of introgression breeding, a genetic infrastructure of exotic libraries can be developed. Such an exotic library comprises a set of introgression lines, each of which has a single, possibly homozygous, marker-defined chromosomal segment that originates from a donor exotic parent, in an otherwise homogenous elite genetic background, so that the entire donor genome would be represented in a set of introgression lines. A collection of such introgression lines is referred as libraries of introgression lines or IL libraries (ILLs). The lines of an ILL cover usually the complete genome of the donor, or the part of interest. Introgression lines allow the study of quantitative trait loci, but also the creation of new varieties by introducing exotic traits. High resolution mapping of QTL using ILLs enable breeders to assess whether the effect on the phenotype is due to a single QTL or to several tightly linked QTL affecting the same trait. In addition, sub-ILs can be developed to discover molecular markers which are more tightly linked to the QTL of interest, which can be used for marker-assisted breeding (MAB). Multiple introgression lines can be developed when the introgression of a single QTL is not sufficient to result in a substantial improvement in agriculturally important traits (Gur and Zamir, Unused natural variation can lift yield barriers in plant breeding, 2004, PLOS Biol.; 2 (10): e245).

Tissue Culture

As it is well known in the art, tissue culture of tomato can be used for the in vitro regeneration of tomato plants. Tissues cultures of various tissues of tomato and regeneration of plants therefrom are well known and published. By way of example, a tissue culture comprising organs has been used to produce regenerated plants as described in Girish-Chandel et al., Advances in Plant Sciences. 2000, 13:1, 11-17, Costa et al., Plant Cell Report. 2000, 19:3327-332, Plastira et al., Acta Horticulturae. 1997, 447, 231-234, Zagorska et al., Plant Cell Report. 1998, 17:12 968-973, Asahura et al., Breeding Science. 1995, 45:455-459, Chen et al., Breeding Science. 1994, 44:3, 257-262, Patil et al., Plant and Tissue and Organ Culture. 1994, 36:2,255-258. It is clear from the literature that the state of the art is such that these methods of obtaining plants are routinely used and have a very high rate of success. Thus, another aspect of this disclosure is to provide cells which upon growth and differentiation produce tomato plants having all of the physiological and morphological characteristics of hybrid tomato plant EL ROSILLO.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollens, flowers, seeds, leaves, stems, roots, root tips, anthers, pistils, meristematic cells, axillary buds, ovaries, seed coats, endosperms, hypocotyls, cotyledons and the like. Means for preparing and maintaining plant tissue culture are well known in the art. By way of example, a tissue culture comprising organs has been used to produce regenerated plants. U.S. Pat. Nos. 5,959,185, 5,973, 234, and 5,977,445 describe certain techniques, the disclosures of which are incorporated herein by reference.

EXAMPLES

The foregoing examples of the related art and limitations related therewith are intended to be illustrative and not exclusive. Other limitations of the related art will become apparent to those of skill in the art upon a reading of the specification.

Development of New EL ROSILLO Tomato Variety

Breeding History of EL ROSILLO

Hybrid tomato plant EL ROSILLO has superior characteristics. The female TOM3082PL and male TOM3040PL parents were crossed to produce hybrid (F1) seeds of EL ROSILLO. The seeds of EL ROSILLO can be grown to produce hybrid plants and parts thereof. The hybrid EL ROSILLO can be propagated by seeds produced from crossing tomato inbred line TOM3082PL with tomato inbred line TOM3040PL or vegetatively.

The origin and breeding history of hybrid plant EL ROSILLO can be summarized as follows: the line TOM3082PL was used as the female plant and crossed by pollen from the line TOM3040PL (both proprietary lines owned by HM.CLAUSE, Inc.). The first trial planting of this hybrid was done in Sinaloa, Mexico in two different locations, Los Mochis and Culiacan during the fall-winter season of the first year of development. The hybrid was further trialed for two additional years, an example of such trial being disclosed in Tables 2 and 3.

The inbred line TOM3082PL is a parent with a medium vine, produces large size fruits, with blocky (oblong) shape. This inbred line was used as female parent in this cross.

The inbred TOM3040PL is a parent with strong vine and medium fruit, with elongated fruit shape. It was used as the male parent in this cross.

Hybrid tomato plant EL ROSILLO compares with TEMIBLE, a commercial variety in Mexico. Despite having a similar profile in the same country, there are significant differences between EL ROSILLO and TEMIBLE, including the plant vigor, continuity of setting, fruit cover, and yield measured by number and weight of fruits (Tables 2 and 3).

Some of the criteria used to select the hybrid EL ROSILLO as well as their inbred parent lines in various generations include: plant vigor, fruit size, fruit firmness, fruit shape, and disease resistances. Additionally, fruit yield data was used to select the hybrid.

Hybrid tomato plant EL ROSILLO has shown uniformity and stability for the traits, within the limits of environmental influence for the traits as described in the following Variety Descriptive Information. No variant traits have been observed or are expected for important agronomical traits in tomato hybrid EL ROSILLO.

Hybrid tomato plant EL ROSILLO has the following morphologic and other characteristics, as compared to TEMIBLE (based primarily on data collected in Los Mochis, Sinaloa, Mexico, all experiments done under the direct supervision of the applicant).

TABLE 1

| Traits | | EL ROSILLO | TEMIBLE |
| --- | --- | --- | --- |
| 1. Seed-propagated varieties only: Seedling: anthocyanin coloration of hypocotyl | absent, present | present | present |
| 2. Plant: Growth type | determinate, indeterminate | determinate | determinate |
| 3. Only determinate varieties: Plant: Number of inflorescence on main stem | few, medium, many | medium | medium |
| 4. Stem: anthocyanin coloration | absent or very weak, weak, medium, strong, very strong | medium | absent or very weak |
| 5. Only indeterminate varieties: Stem: Length of internode | short, medium, long | — | — |
| 6. Only indeterminate varieties: Plant: Height | very short, short, medium, long, very long | — | — |
| 7. Leaf: Attitude | erect, semi-erect, horizontal, semi-drooping, drooping | semi-erect | semi-erect |
| 8. Leaf: Length | short, medium, long | medium | medium |
| 9. Leaf: Width | narrow, medium, broad | medium | broad |
| 10. Leaf: Type of blade | pinnate, bipinnate | bipinnate | bipinnate |
| 11. Leaf: Size of leaflets | very small, small, medium, large, very large | medium | large |
| 12. Leaf: Intensity of green color | light, medium, dark | light | medium |
| 13. Leaf: Glossiness | weak, medium, strong | weak | weak |
| 14. Leaf: Blistering | weak, medium, strong | weak | weak |
| 15. Leaf: Attitude of petiole of leaflet in relation to main axis | semi-erect, horizontal, semi-drooping | semi-erect | horizontal |
| 16. Inflorescence: Type | mainly uniparous, equally uniparous and multiparous, mainly multiparous | mainly uniparous | equally uniparous and multiparous |
| 17. Flower: Color | yellow, orange | yellow | yellow |
| 18. Flower: Pubescence of style | absent, present | absent | present |
| 19. Peduncle: abscission layer | absent, present | present | present |
| 20. Only varieties with peduncle abscission layer: Pedicel length | short, medium, long | medium | medium |
| 21. Fruit: Green shoulder (before maturity) | absent, present | absent | absent |
| 22. Fruit: Extent of green shoulder (before maturity) | very small, small, medium, large | — | — |

TABLE 1-continued

| Traits | | EL ROSILLO | TEMIBLE |
|---|---|---|---|
| 23. Fruit: Intensity of green color of shoulder (before maturity) | light, medium, dark | — | — |
| 24. Fruit: Intensity of green color excluding shoulder (before maturity) | very light, light, medium, dark, very dark | light | light |
| 25. Fruit: Green stripes (before maturity) | absent, present | absent | absent |
| 26. Fruit: Size | very small, small, medium, large, very large | medium | medium |
| 27. Fruit: Ratio length/diameter | very compressed, moderately compressed, medium, moderately elongated, very elongated | moderately elongated | moderately elongated |
| 28. Fruit: Shape in longitudinal section | flattened, oblate, circular, oblong, cylindric, elliptic, cordate, ovate, obovate, pyriform, obcordate | cylindric | obovate |
| 29. Fruit: Ribbing at peduncle end | absent or very weak, weak, medium, strong, very strong | weak | weak |
| 30. Fruit: Depression at peduncle end | absent or very weak, weak, medium, strong | weak | weak |
| 31. Fruit: Size of peduncle scar | very small, small, medium, large, very large | small | small |
| 32. Fruit: Size of blossom scar | very small, small, medium, large, very large | very small | small |
| 33. Fruit: Shape at blossom end | indented, indented to flat, flat, flat to pointed, pointed | flat to pointed | flat |
| 34. Fruit: Diameter of core in cross section in relation to total diameter | very small, small, medium, large, very large | medium | small |
| 35. Fruit: Thickness of pericarp | very thin, thin, medium, thick, very thick | thick | medium |
| 36. Fruit: Number of locules | only two; two and three; three and four; four, five, or six; more than six | three and four | two and three |
| 37. Fruit: Color at maturity | cream, yellow, orange, pink, red, brown, green | red | red |
| 38. Fruit: Color of flesh (at maturity) | cream, yellow, orange, pink, red, brown, green | red | red |
| 39. Fruit: Glossiness of skin | weak, medium, strong | weak | strong |
| 40. Fruit: Color of epidermis | colorless, yellow | yellow | yellow |
| 41. Fruit: Firmness | very soft, soft, medium, firm, very firm | firm | firm |
| 42. Fruit: Shelf-life | very short, short, medium, long, very long | medium | medium |
| 43. Time of flowering | early, medium, late | medium | medium |
| 44. Time of maturity | very early, early, medium, late, very late | medium | medium |
| 45. Sensitivity to silvering | insensitive, sensitive | sensitive | insensitive |
| 46a. Resistance to *Meloidogyne incognita* (Mi) | susceptible, moderately resistant, highly resistant | moderately resistant | moderately resistant |
| 46b. Resistance to *Meloidogyne arenaria* (Ma) | susceptible, moderately resistant, highly resistant | moderately resistant | moderately resistant |
| 46c. Resistance to *Meloidogyne javanica* (M) | susceptible, moderately resistant, highly resistant | moderately resistant | moderately resistant |
| 47. Resistance to *Verticillium* sp. (Va and Vd) - Race 0 | absent, present | present | present |
| 48.1 Resistance to *Fusarium oxysporum* f. sp. *lycopersici* (Fol) - Race 0 (ex 1) | absent, present | present | present |
| 48.2 Resistance to *Fusarium oxysporum* f. sp. *lycopersici* (Fol) - Race 1 (ex 2) | absent, present | present | present |
| 48.3 Resistance to *Fusarium oxysporum* f. sp. *lycopersici* (Fol) - Race 2 (ex 3) | absent, present | present | absent |
| 49. Resistance to *Fusarium oxysporum* f. sp. *radicis-lycopersici* (Forl) | absent, present | absent | absent |
| 50.1 Resistance to *Fulvia fulva* (Ff) (ex *Cladosporium fulvum*) - | absent, present | absent | absent |

TABLE 1-continued

| Traits | | EL ROSILLO | TEMIBLE |
|---|---|---|---|
| Race 0 | | | |
| 50.2 Resistance to *Fulvia fulva* (Ff) (ex *Cladosporium fulvum*) - Group A | absent, present | absent | absent |
| 50.3 Resistance to *Fulvia fulva* (Ff) (ex *Cladosporium fulvum*) - Group B | absent, present | absent | absent |
| 50.4 Resistance to *Fulvia fulva* (Ff) (ex *Cladosporium fulvum*) - Group C | absent, present | absent | absent |
| 50.5 Resistance to *Fulvia fulva* (Ff) (ex *Cladosporium fulvum*) - Group D | absent, present | absent | absent |
| 50.6 Resistance to *Fulvia fulva* (Ff) (ex *Cladosporium fulvum*) - Group E | absent, present | absent | absent |
| 51.1 Resistance to Tomato mosaic virus (ToMV) - Strain 0 | absent, present | absent | absent |
| 51.2 Resistance to Tomato mosaic virus (ToMV) - Strain 1 | absent, present | absent | absent |
| 51.3 Resistance to Tomato mosaic virus (ToMV) - Strain 2 | absent, present | absent | absent |
| 52. Resistance to *Phytophthora infestans* (Pi) | absent, present | absent | absent |
| 53. Resistance to *Pyrenochaeta lycopersici* (Pl) | absent, present | absent | absent |
| 54. Resistance to *Stemphylium* spp. (Ss) | absent, present | present | absent |
| 55. Resistance to *Pseudomonas syringae* pv. tomato (Pst) | absent, present | present | present |
| 56. Resistance to *Ralsonia solanacearum* (Rs) - Race 1 | absent, present | absent | absent |
| 57. Resistance to Tomato yellow leaf curl virus (TYLCV) | absent, present | present | present |
| 58. Resistance to Tomato spotted wilt virus (TSWV) - Race 0 | absent, present | present | present |
| 59. Resistance to *Leveillula taurica* (Lt) | absent, present | absent | absent |
| 60. Resistance to *Oidium neolycopersici* (On) (ex *Oidium lycopersicum*) | absent, present | absent | absent |
| 61. Resistance to Tomato torrado virus (ToTV) | absent, present | absent | absent |

Example 2-Comparison of New EL ROSILLO Tomato with Check Variety

In the tables that follow (Tables 2 and 3) the traits and characteristics of hybrid tomato plant EL ROSILLO are given compared to another hybrid, the variety TEMIBLE. The data collected are presented for key characteristics and traits. Hybrid tomato EL ROSILLO was tested during multiple growing periods from several field locations, over 3 years, with two or more replications per location. Information about the hybrid, as compared to a check hybrid is presented (based primarily on data collected in Mexico). All experiments were done under the direct supervision of the applicant).

TABLE 2

Horticultural and yield performance of EL ROSILLO compared to commercial check TEMIBLE in Lequeitio, Guanajuato, Mexico. Trial planted on March $1^{st}$ and evaluated on July $7^{th}$

| Hybrid | HLT | VN | CV | FRM | SZ | T N | T W |
|---|---|---|---|---|---|---|---|
| EL ROSILLO | 5.5 | 6 | 5.5 | 5 | 5.8 | 115 | 9.5 |
| TEMIBLE | 5.4 | 5.4 | 5.4 | 5.5 | 5.6 | 88.5 | 7.6 |

HLT = Plant healthiness, VN = Vine vigor, CV = fruit cover, FRM = fruit firmness at red stage, SZ = fruit size, T N = total number of fruits, T W = total weight (Kg) of fruits. Traits HLT, VN, CV, FRM, and SZ were quantified in a 1-9 scale, where 1 = complete absence of the trait, 2 = very bad performance of the trait, 3 = bad performance of the trait, 4 = performance below expectation, 5 = performance closer to ideal, 6 = good performance of the trait, 7 = very good performance, 8 = excellent performance, 9 = exceptional performance.

HLT=Plant healthiness, VN=Vine vigor, CV=fruit cover, FRM=fruit firmness at red stage, SZ=fruit size, T N=total number of fruits, T W=total weight (Kg) of fruits. Traits HLT, VN, CV, FRM, and SZ were quantified in a 1-9 scale, where 1-complete absence of the trait, 2=very bad performance of the trait, 3=bad performance of the trait, 4=performance below expectation, 5=performance closer to ideal, 6=good performance of the trait, 7=very good performance, 8=excellent performance, 9=exceptional performance.

TABLE 3

Horticultural and yield performance of EL ROSILLO compared to commercial check TEMIBLE in Tequisquiapan, Queretaro, Mexico. Trial planted on March $1^{st}$ and evaluated on July $1^{st}$

| Hybrid | HLT | VN | CV | FRM | SZ | T N | T W |
|---|---|---|---|---|---|---|---|
| EL ROSILLO | 5 | 6 | 6.5 | 7 | 5.5 | 145 | 10.35 |
| TEMIBLE | 4.7 | 5.3 | 5.5 | 5.8 | 5.6 | 67.3 | 4.67 |

HLT = Plant healthiness, VN = Vine vigor, CV = fruit cover, FRM = fruit firmness at red stage, SZ = fruit size, T N = total number of fruits, T W = total weight (Kg) of fruits. Traits HLT, VN, CV, FRM, and SZ were quantified in a 1-9 scale, where 1 = complete absence of the trait, 2 = very bad performance of the trait, 3 = bad performance of the trait, 4 = performance below expectation, 5 = performance closer to ideal, 6 = good performance of the trait, 7 = very good performance, 8 = excellent performance, 9 = exceptional performance.

HLT=Plant healthiness, VN=Vine vigor, CV=fruit cover, FRM=fruit firmness at red stage, SZ=fruit size, T N=total number of fruits, T W=total weight (Kg) of fruits. Traits HLT, VN, CV, FRM, and SZ were quantified in a 1-9 scale, where 1=complete absence of the trait, 2=very bad performance of the trait, 3=bad performance of the trait, 4=performance below expectation, 5=performance closer to ideal, 6=good performance of the trait, 7=very good performance, 8=excellent performance, 9=exceptional performance.

Deposit Information

A deposit of the tomato seed of this disclosure is maintained by HM.CLAUSE, Inc. Davis Research Station, 9241 Mace Boulevard, Davis, California 95618. In addition, a sample of the hybrid tomato seed of this disclosure has been deposited with the National Collections of Industrial, Food and Marine Bacteria (NCIMB), NCIMB Ltd. Wellheads Place, Dyce, Aberdeen AB21 7 GB To satisfy the enablement requirements of 35 U.S.C. 112, and to certify that the deposit of the tomato seed of the present disclosure meets the criteria set forth in 37 CFR 1.801-1.809, Applicants hereby make the following statements regarding the deposited hybrid tomato EL ROSILLO (deposited as NCIMB Accession No. 44695 on Oct. 28, 2025).

1. During the pendency of this application, access to the disclosure will be afforded to the Commissioner upon request;
2. All restrictions on availability to the public will be irrevocably removed upon granting of the patent under conditions specified in 37 CFR 1.808;
3. The deposit will be maintained in a public repository for a period of 30 years or 5 years after the last request or for the effective life of the patent, whichever is longer;
4. A test of the viability of the biological material at the time of deposit will be conducted by the public depository under 37 CFR 1.807; and
5. The deposit will be replaced if it should ever become unavailable.

Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 625 seeds of the same variety with the NCIMB.

INCORPORATION BY REFERENCE

All references, articles, publications, patents, patent publications, and patent applications cited herein are incorporated by reference in their entireties for all purposes.

However, mention of any reference, article, publication, patent, patent publication, and patent application cited herein is not, and should not be taken as an acknowledgment or any form of suggestion that they constitute valid prior art or form part of the common general knowledge in any country in the world.

What is claimed is:

1. A seed of hybrid tomato designated EL ROSILLO, wherein a representative sample of seed of said hybrid has been deposited under NCIMB No. 44695.

2. A tomato plant, a part thereof, or a cell thereof, produced by growing the seed of claim 1, wherein the tomato plant produced by growing the seed and a tomato plant produced from the part or the cell have all of the physiological and morphological characteristics of hybrid tomato designated EL ROSILLO when grown under the same environmental condition.

3. The tomato plant, the part thereof, or the cell thereof of claim 2, wherein the part is selected from the group consisting of a leaf, a flower, a fruit, a stalk, a root, a rootstock, a scion, a meristem, and a cell.

4. A tissue culture of regenerable cells produced from the tomato plant or the part thereof of claim 2, wherein a tomato plant regenerated from the tissue culture has all of the physiological and morphological characteristics of hybrid tomato designated EL ROSILLO when grown under the same environmental condition.

5. A tomato plant regenerated from the tissue culture of claim 4.

6. A method for producing a tomato fruit, the method comprising: (a) growing the tomato plant of claim 2 to produce a tomato fruit, and (b) harvesting said tomato fruit.

7. A method for producing a tomato seed, the method comprising: (a) crossing a first tomato plant with a second tomato plant and (b) harvesting the resultant tomato seed, wherein said first tomato plant and/or second tomato plant is the tomato plant of claim 2.

8. A method for producing a tomato seed, the method comprising: (a) self-pollinating the tomato plant of claim 2 and (b) harvesting the resultant tomato seed.

9. A method of vegetatively propagating the tomato plant of claim 2, the method comprising: (a) collecting a part capable of being propagated from the plant of claim 2 and (b) regenerating a plant from said part.

10. The method of claim 9, further comprising (c) harvesting a fruit from said regenerated plant.

11. A plant obtained from the method of claim 9, wherein said plant has all of the physiological and morphological characteristics of hybrid tomato designated EL ROSILLO deposited under NCIMB No. 44695.

12. A tomato fruit selected from: (a) a tomato fruit produced from the plant of claim 2; (b) a tomato fruit produced by the method of claim 6, and (c) a tomato fruit produced from the method of claim 9.

13. A method of producing a tomato plant obtained from hybrid tomato designated EL ROSILLO, the method comprising: (a) self-pollinating the tomato plant of claim 2 at least once to produce a progeny tomato plant obtained from hybrid tomato designated EL ROSILLO.

14. The method of claim 13, further comprising the steps of:

(b) crossing the progeny tomato plant obtained from the hybrid tomato designated EL ROSILLO with itself or a second tomato plant to produce a progeny seed of a subsequent generation;

(c) growing a progeny plant from the progeny seed of the subsequent generation;

(d) crossing the progeny plant of the subsequent generation with itself or a second tomato plant to produce a tomato plant derived from the hybrid tomato designated EL ROSILLO; and (e) repeating step (c) and (d) for at least one generation to produce a tomato plant further derived from the hybrid tomato designated EL ROSILLO.

15. A method of producing a tomato plant obtained from hybrid tomato designated EL ROSILLO, the method comprising: (a) crossing the tomato plant of claim 2 with a second tomato plant to produce a progeny tomato plant obtained from hybrid tomato designated EL ROSILLO.

16. The method of claim 15, further comprising the steps of:

(b) crossing the progeny tomato plant obtained from the hybrid tomato plant designated EL ROSILLO with itself or a second tomato plant to produce a progeny seed of a subsequent generation;

(c) growing a progeny plant from the progeny seed of the subsequent generation;

(d) crossing the progeny plant of the subsequent generation with itself or a second tomato plant to produce a tomato plant derived from the tomato hybrid tomato plant designated EL ROSILLO; and (e) repeating step (c) and (d) for at least one generation to produce a tomato plant further derived from the hybrid tomato plant designated EL ROSILLO.

17. A method of producing a plant of hybrid tomato designated EL ROSILLO comprising at least one desired trait, the method comprising introducing a single locus conversion conferring the desired trait into hybrid tomato designated EL ROSILLO, whereby a plant of hybrid tomato designated EL ROSILLO comprising the desired trait is produced, wherein a representative sample of seed of said hybrid has been deposited under NCIMB No. 44695.

18. A tomato plant, a part thereof, or a cell thereof, produced by the method of claim 17, wherein the plant, the part, or the cell thereof comprises one single locus conversion and otherwise all of the physiological and morphological characteristics of hybrid tomato designated EL ROSILLO deposited under NCIMB No. 44695, wherein the single locus conversion is introduced into the plant by a genetic transformation or a gene editing technique with a nuclease selected from the group consisting of Zinc finger nuclease (ZFN), Transcription Activation-Like Effector Nuclease (TALEN), Clustered Regularly Interspaced Short Palindromic Repeats-associated Cas endonuclease (CRISPR-Cas), meganuclease, homing endonuclease, and RNA-guided nuclease.

19. The plant of claim 18, wherein the single locus conversion confers said plant with male sterility, male fertility, herbicide resistance, insect resistance, disease resistance, water stress tolerance, heat tolerance, improved standability, enhanced plant vigor, improved shelf life, delayed senescence or controlled ripening, or increased nutritional quality.

20. The plant of claim 18, wherein the single locus conversion is an artificially mutated gene or an artificially mutated nucleotide sequence.

21. A method of producing a tomato plant, the method comprising: grafting a rootstock or a scion of the hybrid tomato plant of claim 2 to another tomato plant.

22. A method for producing nucleic acids, the method comprising: isolating nucleic acids from the plant of claim 2, a part, or a cell thereof.

23. A method for producing a second tomato plant, the method comprising applying plant breeding techniques to the plant or part of claim 2 to produce the second tomato plant.

24. A method of producing a commodity plant product, the method comprising obtaining the plant of claim 2 or a part thereof and producing said commodity plant product therefrom.

* * * * *